Figure 1:
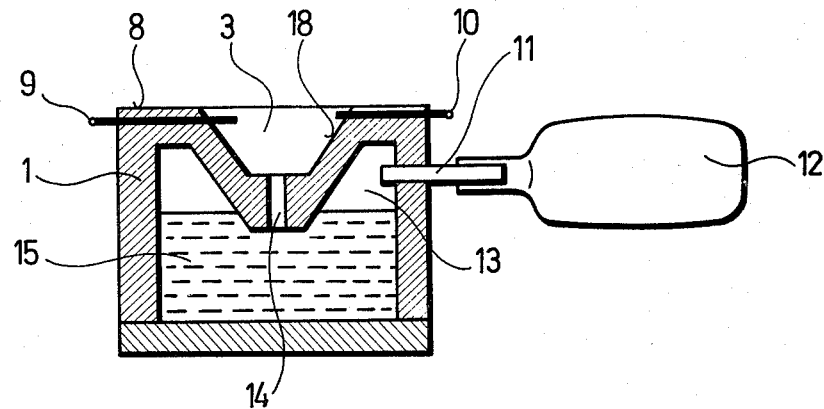

United States Patent [19]

Frenyo

[11] 3,961,895

[45] June 8, 1976

[54] PROCESS AND EQUIPMENT FOR THE DETERMINATION OF CERTAIN COMPONENTS, PARTICULARLY THE CARBON DIOXIDE CONTENT OF GAS MIXTURE

[75] Inventor: Vilmos Frenyo, Budapest, Hungary

[73] Assignee: Novex Talalmanyfejleszto es Ertekesito Kulkereskedelmi Rt., Budapest, Hungary

[22] Filed: Mar. 17, 1975

[21] Appl. No.: 559,044

[30] Foreign Application Priority Data

June 26, 1974 Hungary.............................. NO 184

[52] U.S. Cl............................. 23/232 E; 23/254 E; 324/30 B
[51] Int. Cl.$^2$................... G01N 27/06; G01N 31/06
[58] Field of Search........... 23/232 E, 254 E, 255 E; 324/30 B, 30 R

[56] References Cited
UNITED STATES PATENTS

| | | | |
|---|---|---|---|
| 1,475,000 | 11/1923 | Cooper et al. | 23/255 E |
| 2,953,441 | 9/1960 | Clauss | 23/232 E X |
| 3,660,034 | 2/1972 | Baranyi et al. | 23/232 E X |

Primary Examiner—Robert M. Reese
Attorney, Agent, or Firm—Young & Thompson

[57] ABSTRACT

A component of a gaseous mixture, particularly carbon dioxide, can be measured in extremely small quantities or concentrations, by supporting on a solid surface a thin film of a liquid, e.g. an aqueous solution of barium hydroxide, which reacts with the gaseous component so as substantially to alter the electrical resistance of the solution. The electric resistance of the film is measured between electrodes, before and after exposure to the test gas. The test is much more sensitive than if a confined body of liquid were used as the test solution.

6 Claims, 3 Drawing Figures

U.S. Patent  June 8, 1976  3,961,895

PROCESS AND EQUIPMENT FOR THE DETERMINATION OF CERTAIN COMPONENTS, PARTICULARLY THE CARBON DIOXIDE CONTENT OF GAS MIXTURE

The subjects of the invention are a process and an apparatus whereby the quantity of the individual components of gas mixtures can be readily determined. Determination of the carbon dioxide content is of a particularly great practical importance, thus the solution according to the invention applies above all to this field.

The process and apparatus of the invention are aimed mainly at the task of indicating the carbon dioxide quantity produced by organisms and organic substances, and of precisely defining this quantity. The solution of such a problem is required, for example, when attempting to determine the carbon dioxide production by part of the skin surface of the human body, or by fruits and other plant parts. The invention may have numerous other application possibilities like the determination of the carbon dioxide content of the air, indication of the carbon dioxide quantity produced in the course of certain industrial processes, etc.

The carbon dioxide quantity must often be determined at the site of its production, and in such a manner as to prevent any damage to the object responsible for its production, during the entire test or measurement process. As an example, the storability of certain fruit varieties depends on their ripeness when stored. From storage aspects the optimum ripeness of the fruit depends, in turn, on the carbon dioxide quantity emitted thereby. In order to determine the optimum fruit harvest time, therefore, its carbon dioxide emission must be examined. This test should be performed in the orchard or plantation, with the crop still unharvested. This example proves that certain tests require the performance of serial measurements, sometimes under very unfavourable conditions, far away from electric mains, laboratory and other technical facilities. These requirements can be met only if the measurement method is, with respect to both its technique and the equipment involved, quite simple, readily completed at a rapid rate, and does not demand the satisfaction of technical preconditions from the environment. Further characteristics of an optimum such solution include that no highly qualified skilled labor should be needed, the equipment should be small in size and lightweight, and its transport as well as operation should not lead readily to damage thereto.

There are some methods and facilities existing, particularly for industrial purposes, whereby certain components of the gas mixtures can be identified and their concentration determined. Such a solution is represented, for example, by the Orsat system. These solutions, however, require facilities difficult to operate, and their measurement inaccuracies do not permit the high precision quantitative determination of very low concentration components or gases produced in a very small quantity.

A typical well-known apparatus for similar purposes is the Warburg respirometer, suitable for the examination of the respiration intensity of cells, as based either on the oxygen consumption or the carbon dioxide emission. This device includes an U-manometer to whose legs are connected the receptacles containing the tissues under test. The quantity of the oxygen consumed or the carbon dioxide produced can then be determined on the basis of the differential pressure variation between the manometer legs, due to the oxygen consumption or carbon dioxide production by the tissue parts tested. Since the equipment is operating on a manometric principle, a constant temperature must be maintained during the entire measurement period which, in turn, requires the use of a 10 to 25 lit. water tank. Thus its total weight is 20 to 50 kg, it works with a complicated temperature control, requires current from mains, is not suitable for on site measurements, and cannot be used for example to measure the carbon dioxide emission by a part of the skin surface or a fruit surface section.

Another well-known solution makes use of the absorption of infra red rays for measurement purposes, like the URAS unit, in which the gas under test is circulated, and the carbon dioxide content is determined by measuring the temperature increase due to the infra red absorption. This device, too, can be used only under laboratory conditions, and is not suitable, even under such circumstances, for the accomplishment of tasks like those described above e.g. the measurement of the carbon dioxide quantity produced by a small part of the living skin surface, or by a fruit.

Eudiometers, too, are used for the purpose, but these are best suited for gas volume measurements and, as such, are not adaptable for the solution of the problems referred to above.

The solutions based on chemical titration also deserve mention, of which the Pettenkoffer and Winkler methods have been widely accepted. Essentially, these methods make the liquid employed absorb the gas tested, or certain components thereof, and the quantity of the gas thus absorbed will then be measured. Accordingly they are not suitable, either, for the solution of the problems described above.

The method and apparatus according to the present invention have eliminated all the disadvantages and deficiencies of the known solutions, as far as the accomplishment of the tasks indicated is concerned.

In the process according to the invention the gas under test is contacted with a liquid reagent whose electrical resistance will change because of its transformation due to the carbon dioxide effect. It is actually an electrical resistance measurement wherefrom, however, the carbon dioxide quantity may be deduced, as the scale of the resistance gauge can be calibrated directly for the carbon dioxide quantity or concentration. For the implementation of the process it is absolutely immaterial whether a sample is taken from the gas mixture tested, and this sample is contacted with the liquid reagent or the latter, together with the electrodes, is located in the gas space without sampling.

The essential part of the process invented is the formation of a liquid film consisting of the reagent, between the electrodes, whereafter either a sample of the gas tested or the entire gas space proper is contacted with this liquid film, in order to measure the resistance variation between the electrodes, from which the carbon dioxide content of the gas mixture under test can then be determined.

The liquid reagent film may be formed over the surface between the electrodes, or a reagent carrier may be located between them to hold even a minute quantity thereof. This carrier may be a capillary, or for example a thread that can hold over its surface a continuous liquid film.

When selecting the reagent, a stable compound should be preferred in which, upon the effect exerted by the carbon dioxide, a rapid rate transformation could take place whereby the electrical resistance of the liquid reagent would change. The aqueous solution of barium hydroxide is, for example, excellently suitable for this purpose since in this case the electrical resistance of the original reagent would be greatly increased by the barium carbonate produced upon the carbon dioxide effect. As the reagent in the form of a liquid film is of only a very small quantity, a similarly very small gas mixture volume or extremely low carbon dioxide concentration will also provide, within a short period of time, for the chemical transformation resulting in a change of the electrical resistance.

If barium hydroxide reagent is used, in order to prevent any further reaction decreasing the electrical resistance after the chemical transformation referred to, it is advisable to add a priori a solution containing lithium carbonate to the reagent, and also another additive whereby the adhesion of the liquid film to the surface between the electrodes would be promoted.

If a gas other than carbon dioxide is to be identified, naturally another liquid reagent should be used as required, but it certainly will not change the essential features of the process invented, if a reagent other than that mentioned above as an example is used for the identification of carbon dioxide.

The process according to the present invention, thus consists of taking a sample from the gas mixture under test, whereafter or prior thereto a film of the liquid reagent is formed between the electrodes, with the gas space to be tested directly contacted with the area enclosed by one side of said film and, as the final step, the carbon dioxide content of the gas mixture is then determined from the measured values of the resistance variation between the electrodes.

The essential characteristics of the associated equipment are, on the other hand, that it has a liquid reagent film retainer surface, electrodes connected to this surface and, if needed, a sample holder readily opened and closed, connected in a sealed manner to the device containing said liquid film.

In a preferred construction of the apparatus the surface retaining the liquid reagent in a membrane form is replaced by a component e.g. thread carrying a predetermined liquid reagent quantity between the electrodes.

Figure 2:
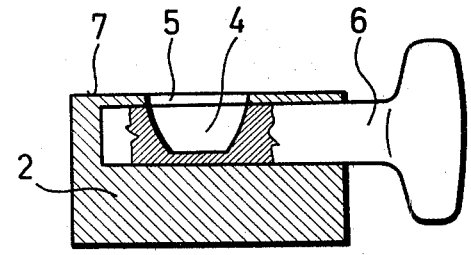
Figure 3:
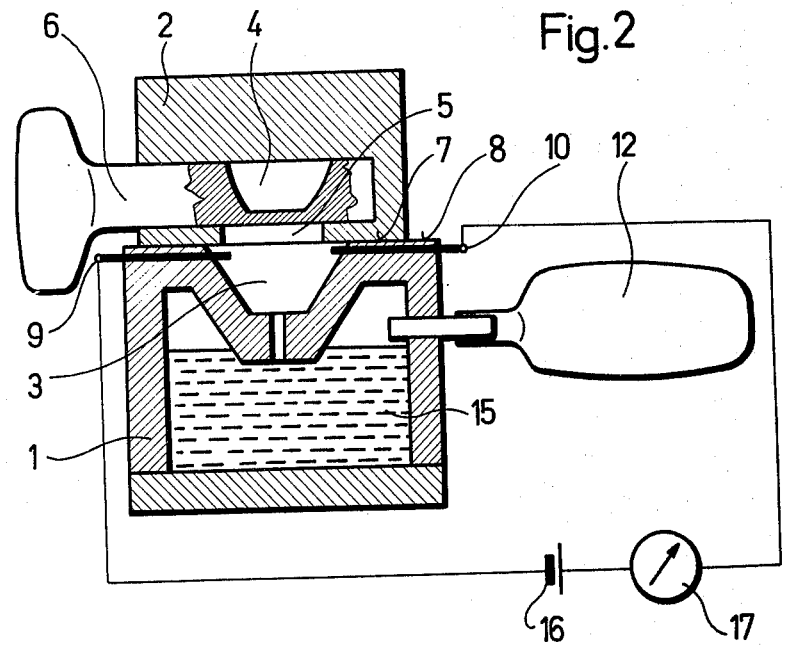

The process and apparatus are described in detail by means of the Figures of the attached drawing, illustrating an exemplary construction of the equipment, where FIG. 1 illustrates a sectional view of the equipment, FIG. 2 presents a sectional view of the sample holder, and FIG. 3 shows the equipment parts depicted in FIGS. 1 and 2, in assembled condition during measurement.

In FIG. 1 a body 1 is a hollow vessel having a funnel shaped part protruding therein. Below the fitting plane 8 of the top part of the said body 1 there is a die 3 developed at the funnel, whose bottom has a bore 14 perforating the funnel wall. The wall of the body 1 has electrodes 9 and 10 built in gastightly, in such a manner as to have their inside ends protrude at least to the surface 18 of said die 3 or somewhat beyond it. A liquid reagent 15 is in this body 1, covering the lower orifice of a bore 14, but not filling up the entire cavity, whereby an air space 13 will be created above the reagent 15. This air space 13 opens into a stub 11, to the outer end of which a pressure generator 12 is connected. The latter is a simple rubber ball, but it may be a plastic sleeve, a small-size piston mechanism, etc.

A sample holder 2 according to FIG. 2 may be a solid block, whose bore has a locking element 6 fitted in a sealed but rotary manner. The locking element 6 has a sample space 4, while the wall of the sample holder 2 has an orifice 5, opposite to said sample space 4. A plate 7 bounding said orifice 5 creates a fitting plane. Both the body 1 and the sample holder 2 may be of a size where the length of each edge is not more than a few cm, which means that the equipment has a minimum floor space requirement, being a light-weight portable apparatus. Furthermore, both the body 1 and the sample holder 2 may be made of "Plexiglas, " since this material can be readily formed in a simple manner, and it permits the production of the fitting planes and the locking element in a gastight form.

Operation of the equipment, and the implementation of the process invented are, with respect to FIG. 3, as follows. Let us assume the task of identifying the carbon dioxide quantity emitted by an apple.

The equipment is made ready for use by filling up the body 1 to the required level with the reagent 15, and by connecting a current supply 16 and a resistant instrument 17 to the electrodes 9 and 10.

The locking element 6 of the sample holder 2 is now adjusted to make the open part of the sample space 4 coincide with the position of the orifice 5, then the adapter plane 7 of the sample holder is fitted to the surface of the apple and, finally, the sample space 4 is closed after a few minutes by turning the interlock element 6.

Now the pressure generator 12 is used to provide for an overpressure in the air space 13, whereby the reagent 15 will be transferred into the die 13 via the bore 14 to flood it. When the pressure generator 12 is released again, the reagent returns from the die 3 to the body 1 through the bore 14, but a thin liquid reagent film remains on the surface 18.

The sample holder 2 is now fitted to the body 1 to make the adapter planes 7 and 8 adhere to each other. By closing the circuit of the resistance instrument 17 the carbon dioxide content of the air entrapped in the die 3 can be readily determined. Turning the interlock element 6 and opening the sample space 4 will make the contents of the die 3 and said air space 4 form a gas mixture, whose carbon dioxide content will bring about the chemical transformation of the reagent forming a liquid film over the surface 18 which, in turn, will modify the resistance between the electrodes 9 and 10. From this modified resistance then the carbon dioxide content of the gas in the sample space 4 can be determined by any known method.

The solution of the present invention can be employed without sampling by positioning the body 1 in the test space, whereupon the resistance between the electrodes 9 and 10 is measured by means of the reagent liquid film. In this case the gas mixture tested fills the environment of the body 1, and may directly contact the liquid film over the surface 18.

The apparatus of the invention may be constructed in such a manner that, for example, a piece of thread is inserted between the electrodes 9 and 10, to which the liquid reagent is transferred, whereupon the thread will retain a film over its own surface. The method of measurement is identical here to that described above.

The process and equipment according to the invention are suitable for the identification of an extremely small gas e.g. carbon dioxide quantity, such as the presence of only $10^{-7}$ g carbon dioxide. The solution invented has, at the same time, the extraordinary advantage of being practically independent of the temperature, environmental conditions, and technical possibilities. The operation of the apparatus does not require great skill, and the measurement can be performed within a few minutes.

What we claim is:

1. A process for the determination of the content of a component of a gaseous mixture, comprising supporting on a solid surface a thin film of a liquid reagent that reacts with said component to change the electrical resistance of the reagent, exposing an exposed surface of said film to a gas to be tested for said component, and measuring the variation of electrical resistance of said film.

2. A process as claimed in claim 1, in which said liquid reagent is an aqueous solution of barium hydroxide for measuring carbon dioxide content.

3. A process as claimed in claim 1, in which said solid surface is inclined at an angle to the horizontal thereby to ensure that liquid reagent flows from said surface by gravity thereby to leave on said surface only said thin film.

4. Apparatus for the measurement of a component of a gaseous mixture, comprising means defining a solid surface, means for establishing on said solid surface a thin film of a liquid reagent whose electrical resistance changes in contact with said component, a pair of spaced electrodes immersible in said film, and means for measuring current flow between said electrodes and through said film thereby to determine said component in said gaseous mixture as a function of changing electrical resistivity of said film.

5. Apparatus as claimed in claim 4, said solid surface being inclined to the horizontal thereby to ensure that said liquid reagent in excess of said thin film flows by gravity from said solid surface thereby to leave on said solid surface only said thin film.

6. Apparatus as claimed in claim 4, comprising a hollow body for containing said liquid reagent, means closing the upper side of said hollow body except for a bore whose lower end immerses in said liquid reagent, means to generate pressure within said body thereby to force said reagent up through said bore, said electrodes being disposed on the upper side of said closing means whereby reagent forced up through said bore coats a said solid surface extending between said electrodes to form said thin film between said electrodes, said reagent in excess of that which forms said thin film draining by gravity through said bore upon release of said pressure.

* * * * *